US010092765B2

(12) United States Patent
Kane et al.

(10) Patent No.: US 10,092,765 B2
(45) Date of Patent: Oct. 9, 2018

(54) LABELED IMPLANTABLE MEDICAL DEVICES

(71) Applicant: Cardiac Pacemakers, Inc., St. Paul, MN (US)

(72) Inventors: Michael J. Kane, Roseville, MN (US); Michael Keane, Cashel (IE); John O'Rourke, Co. Tipperary (IE)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

(21) Appl. No.: 15/426,313

(22) Filed: Feb. 7, 2017

(65) Prior Publication Data

US 2017/0143979 A1 May 25, 2017

Related U.S. Application Data

(63) Continuation of application No. 14/492,863, filed on Sep. 22, 2014, now Pat. No. 9,572,994.

(60) Provisional application No. 61/883,237, filed on Sep. 27, 2013.

(51) Int. Cl.
  *A61N 1/375* (2006.01)
  *H01R 13/641* (2006.01)
  *A61N 1/05* (2006.01)
  *A61N 1/362* (2006.01)

(52) U.S. Cl.
  CPC ............ *A61N 1/3752* (2013.01); *A61N 1/05* (2013.01); *A61N 1/362* (2013.01); *H01R 13/641* (2013.01); *H01R 2201/12* (2013.01)

(58) Field of Classification Search
  CPC ...... A61N 1/3752; A61N 1/05; A61N 1/3754; H01R 13/641; H01R 13/5224
  See application file for complete search history.

(56) References Cited

U.S. PATENT DOCUMENTS

| 7,274,963 | B2 * | 9/2007 | Spadgenske | A61N 1/3752 439/909 |
| 9,572,994 | B2 | 2/2017 | Kane et al. | |
| 2003/0100220 | A1 | 5/2003 | Scheiner | |
| 2007/0049985 | A1 | 3/2007 | Kessler et al. | |

(Continued)

FOREIGN PATENT DOCUMENTS

| JP | 2009078153 A | 4/2009 |
| WO | WO-2015047946 A1 | 4/2015 |

OTHER PUBLICATIONS

"U.S. Appl. No. 14/492,863, Non Final Office Action dated Feb. 23, 2016", 22 pgs.

(Continued)

*Primary Examiner* — William Levicky
(74) *Attorney, Agent, or Firm* — Schwegman Lundberg & Woessner, P.A.

(57) ABSTRACT

In general, techniques are described for labeling an implantable medical device (IMD). In one example, an IMD can include a housing including electronic circuitry. The IMD can include a header coupled to the housing and includes a core. The core can define a bore and include a first metal label positioned adjacent to the at least one bore. The IMD includes a lead assembly including at least one lead having a distal end and a proximal end, the at least one lead including a second metal label, the distal end including at least one electrode and the proximal end received within the bore.

14 Claims, 9 Drawing Sheets

(56) References Cited

U.S. PATENT DOCUMENTS

| | | | |
|---|---|---|---|
| 2010/0114210 A1* | 5/2010 | Donofrio | A61N 1/3752 607/5 |
| 2011/0160558 A1 | 6/2011 | Rassatt et al. | |
| 2011/0270065 A1 | 11/2011 | Ternes et al. | |
| 2012/0035616 A1 | 2/2012 | Olsen et al. | |
| 2012/0203321 A1 | 8/2012 | Moffitt et al. | |
| 2013/0218154 A1 | 8/2013 | Carbunaru | |
| 2015/0094792 A1 | 4/2015 | Kane et al. | |

OTHER PUBLICATIONS

"U.S. Appl. No. 14/492,863, Notice of Allowance dated Oct. 7, 2016", 8 pgs.

"U.S. Appl. No. 141492,863, Response filed Feb. 9, 2016 to Restriction Requirement dated Dec. 9, 2015", 10 pgs.

"U.S. Appl. No. 14/492,863, Response filed May 23, 2016 to Non Final Office Action dated Feb. 23, 2016", 21 pgs.

"U.S. Appl. No. 14/492,863, Response filed Sep. 6, 2016 to Restriction Requirement dated Jul. 6, 2016", 8 pgs.

"U.S. Appl. No. 14/492,863, Restriction Requirement dated Jul. 6, 2016", 7 pgs.

"U.S. Appl. No. 14/492,863, Restriction Requirement dated Dec. 9, 2015", 8 pgs.

"Australian Application Serial No. 2014327120, First Examiner Report dated Aug. 12, 2016", 3 pgs.

"Australian Application Serial No. 2014327120, Response filed Dec. 6, 2016 to First Examiner Report dated Aug. 12, 2016", 12 pgs.

"European Application Serial No. 14778036.5, Response filed Oct. 13, 2016 to Communication pursuant to Rules 161(1) and 162 EPC dated May 4, 2016", 29 pgs.

"International Application Serial No. PCT/US2014/056773, International Preliminary Report on Patentability dated Apr. 7, 2016", 7 pgs.

"International Application Serial No. PCT/US2014/056773, International Search Report dated Dec. 10, 2014", 3 pgs.

"International Application Serial No. PCT/US2014/056773, Written Opinion dated Dec. 10, 2014", 5 pgs.

"Chinese Application Serial No. 201480065158.5, Office Action dated Apr. 13, 2017", w/ English translation, 14 pgs.

"Chinese Application Serial No. 201480065158.5, Response filed Aug. 23, 2017 to Office Action dated Apr. 13, 2017", w/ claims in English, 10 pgs.

"Japanese Application Serial No. 2016-516955, Office Action dated Mar. 14, 2017", w/ English translation, 9 pgs.

"Japanese Application Serial No. 2016-516955, Response filed Aug. 9, 2017 to Office Action dated Mar. 14, 2017", w/ claims in English, 9 pgs.

* cited by examiner

LABELED IMPLANTABLE MEDICAL DEVICES

CLAIM OF PRIORITY

This application is a continuation of U.S. application Ser. No. 14/492,863, filed Sep. 22, 2014, which claims the benefit of priority under 35 U.S.C. § 119(e) of U.S. Provisional Patent Application Ser. No. 61/883,237, filed on Sep. 27, 2013, which is herein incorporated by reference in its entirety.

TECHNICAL FIELD

This document relates generally to medical devices and, in particular, to labels for implantable medical devices.

BACKGROUND

Implantable medical devices (IMDs) can perform a variety of diagnostic or therapeutic functions. In an example, an IMD can include one or more cardiac function management features, such as to monitor the heart or to provide electrical stimulation to a heart or to the nervous system. The cardiac function management features can be used to diagnose or treat a subject, for example, in cases of electrical or mechanical abnormalities of the heart. Examples of IMDs can include pacers, automatic implantable cardioverter-defibrillators (ICDs), cardiac resynchronization therapy (CRT) devices, implantable monitors, neuromodulation devices (e.g., deep brain stimulators, or other neural stimulators), cochlear implants, or drug pumps, among other examples.

Such IMDs can include a housing carrying electronic circuitry configured to wirelessly transfer information between implanted IMDs, or between an IMD and an assembly external to the body. Such information can include, for example, programming instructions or configuration information to configure the IMD to monitor, diagnose, or treat a physiologic condition. Such information can also include data sensed, detected, or processed by the IMD and transmitted to another device or assembly (e.g., physiologic information, a disease status, etc.). Electrodes can be connected to the housing via a connective part referred to as a header. The header and the leads have largely been standardized. The header can include a relatively deep female socket (e.g., a bore) having a number of contact surfaces whereas the lead can be provided with a male part comprising one or several corresponding peripheral, generally circular contact surfaces. Each lead has a designated bore, and inserting a lead into an incorrect bore of the header can cause malfunctions of the IMD after implantation.

The leads are electrically connected to the electronic circuitry of the housing via one or more contact wires extending from the housing. The number of contact wires can vary and as the number of contact wire increases, the risk of wire crossing can also increase. Incorrect connection of leads into the bores and wire crossing can cause various errors such as the stimulation or sensing of the wrong chambers of the heart, incomplete or intermittent connectivity between leads and the IMD, or ineffective defibrillation therapy. Correcting the errors can result in extended procedure durations. In some cases, correcting the errors can require subsequent surgical revisions, thereby increasing the patient's risk of morbidity and mortality.

OVERVIEW

Generally, implantable medical devices (IMDs) can include a pacemaker, a defibrillator, a cardiac resynchronization therapy device, a neurostimulation device, an implantable monitoring device, or one or more other devices. An IMD may generate an electrostimulation to be delivered to a desired tissue site. Delivery of the electrostimulation may be via electrodes that may be included as a portion of an implantable lead assembly. The lead assembly may be mechanically and electrically coupled to the IMD to interface with circuitry included in the IMD.

The present inventors have recognized among other things that a proliferation of lead or electrode configurations may complicate coupling the leads to the IMD and complicate the coupling of the electronic circuitry contained within the housing to the leads. For example, each lead is coupled to the IMD such that the lead is electrically coupled to accompanying circuitry contained in the housing. In order to reduce the risk of incorrectly coupling a lead to the header and incorrectly coupling the circuitry, the present inventors have provided a labeling system and method that is low cost and biocompatible.

Previous approaches have incorporated inks to label various components of IMDs. However, in order to incorporate ink for use with IMDs, the inks go through stringent biocompatibility testing. The complexity of ink and pigment systems can increase the cost of biocompatibility verification and product validation. The continuous monitoring of ink and pigment purity can increase the cost of providing a labeling system for IMDs.

Various embodiments of the present disclosure can provide a biocompatible color coded and text labeling system for IMDs. For example, biocompatible metals can be anodized to color the surface without altering the biocompatibility of the material. Anodizing the biocompatible metals does not compromise the integrity and properties of the biocompatible metal and maintains the suitability of the biocompatible metal for use in biomedical applications. In an example, the biocompatible metals can be anodized to provide text to the surface to assist in labeling components of the IMDs. Imparting color and text to various components of the IMDs can assist in identification of parts and reduce the risk of incorrectly manufacturing, assembling, and implanting the IMDs. The benefits of this are advantageous in surgical applications and in the assembly of complex IMDs.

The present disclosure can provide labeling to IMDs by including biocompatible metal substrates that have been anodized to provide an identifier including at least one of color and text. The anodized biocompatible metal substrates are biocompatible and can reduce the risk of incorrect assembly such as wire crossing and incorrectly coupling leads. The labels and methods described herein can eliminate an unstable component (e.g., ink) and eliminate the biocompatibility risk of using other labeling methods. Additionally, the IMDs and methods described herein have flexible manufacturing and a low cost of implementation.

BRIEF DESCRIPTION OF THE DRAWINGS

In the drawings, which are not necessarily drawn to scale, like numerals may describe similar components in different views. Like numerals having different letter suffixes may represent different instances of similar components.

The drawings illustrate generally, by way of example, but not by way of limitation, the various examples discussed in the present document.

DETAILED DESCRIPTION

Figure 1:
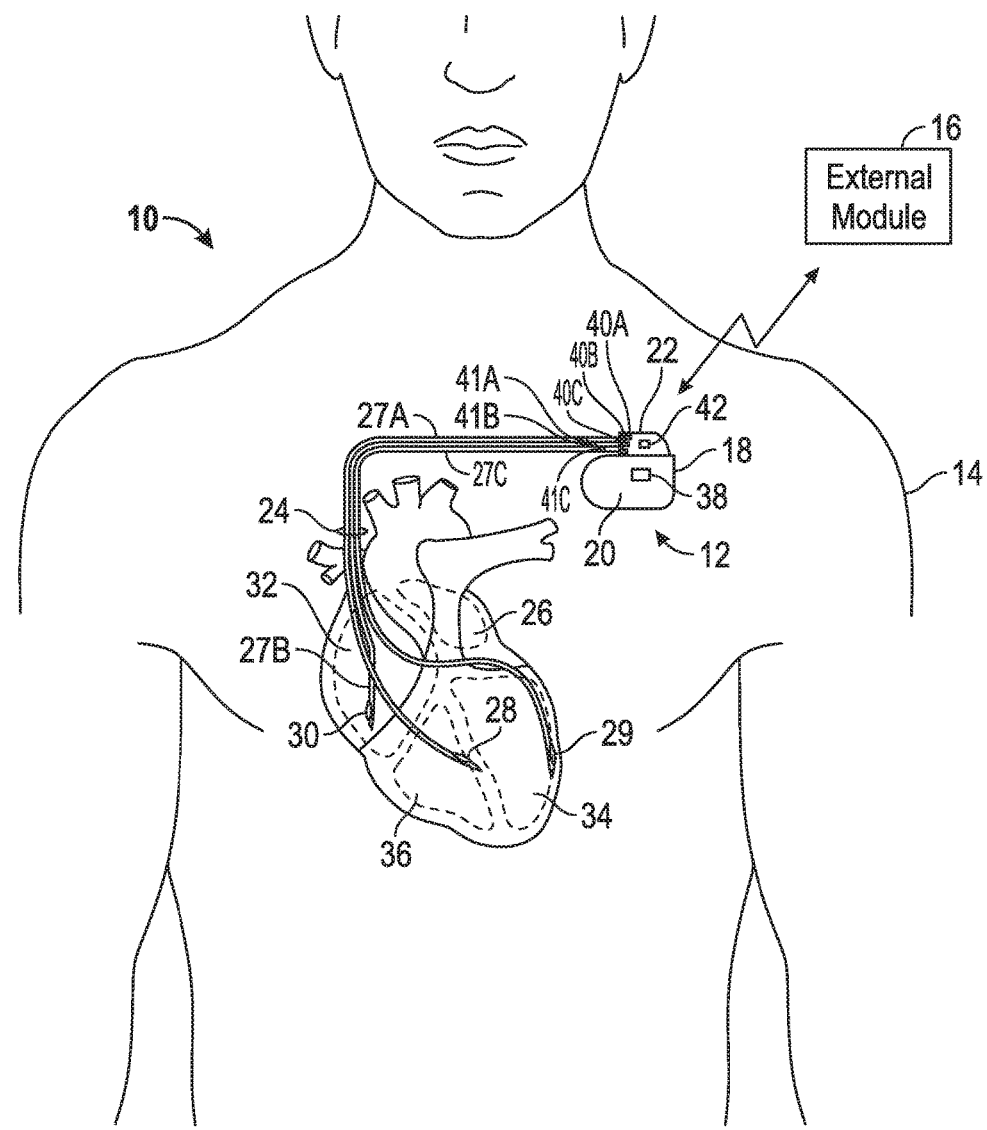
FIG. 1 illustrates generally an example of a system including an IMD.

FIG. 1 illustrates generally an example of a system 10 that can include an implantable medical device (IMD) 12 implanted within a body (e.g., a patient 14), wirelessly coupled to an external module 16. In an example, the IMD 12 can include an implantable device housing 18 including a conductive portion (e.g., a hermetically-sealed titanium housing, or a housing including one or more other materials), a header 22, and one or more implantable lead assemblies 24. The header 22 can mechanically and electrically couple the one or more implantable lead assemblies 24 to the housing 18 and electrical circuitry contained in the housing 18.

In an example, the IMD 12 may be coupled to one or more implantable lead assemblies, such as one or more intravascularly-deliverable lead assemblies 24. The one or more lead assemblies 24 may be configured to provide electrostimulation to one or more sites on, within, or near a heart 26. For example, such lead assemblies 24 may include multiple leads 27A, 27B, and 27C (collectively referred to as "leads 27"). The leads 27 can include one or more electrodes.

For example, lead 27A may include electrode 28 associated with right ventricle 36, such as tip electrode and/or a ring electrode. The electrode 28 is "associated" with the particular heart chamber by inserting it into that heart chamber, by inserting it into a portion of the heart's vasculature that is close to that heart chamber, by epicardially placing the electrode outside that heart chamber, or by any other technique of configuring and situating an electrode for sensing signals and/or providing therapy with respect to the heart chamber. Lead 27B can include electrode 30 associated with the right atrium 32, such as tip electrode and/or ring electrode. Lead 27C, which can be introduced into the coronary sinus and/or the great cardiac vein or one of its tributaries, can include electrode 29 associated with left ventricle 34, such as tip electrode and/or ring electrode. While the example in FIG. 1 includes three leads configured to be positioned within the heart, the number and location of the leads can vary depending on the type of therapy to be provided and the type of IMD.

In an example, the IMD 12 may include one or more electrodes located on the housing 18 of the IMD 12, such as housing electrode 38 and/or header electrode 42, which are useful for, among other things, unipolar sensing of heart signals or unipolar delivery of contraction-evoking stimulations in conjunction with one or more of the electrodes 28, 29, and 30 associated with heart 26.

The housing 18 can contain at least a portion of an implantable circuitry 20, such as a transmitter, a receiver, or a transceiver. In an example, the IMD 12 can include a header 22 that is configured to mechanically and electrically couple the one or more lead assemblies 24 to the implantable circuitry 20 of the housing 18. The IMD 12 can include an antenna within the header 22 configured to wirelessly transfer information electromagnetically to an external module 16. In an example, the external module 16 can include an external antenna coupled to an external telemetry circuit.

In an example, the external module 16 can include a physician programmer, a bedside monitor, or other relatively nearby assembly used to transfer programming instructions or configuration information to the IMD 12, or to receive diagnostic information, a disease status, information about one or more physiologic parameters, or the like, from the IMD 12. The external module 16 can be communicatively connected to one or more other external assemblies, such as a remote external assembly, located elsewhere (e.g., a server, a client terminal such as a web-connected personal computer, a cellular base-station, or another wirelessly-coupled or wired remote assembly).

As discussed herein, the proliferation of lead and electrode configurations can complicate coupling the leads 27 to the housing 18 via the header 22. In the example of FIG. 1, the header 22 can include header labels 40A-C (collectively referred to herein as "header labels 40") and the leads 27 can include lead labels 41A-C (collectively referred to herein as "lead labels 41"). The header and lead labels 40 and 41 can be made from a biocompatible material such as a biocompatible metal substrate. For example, the header and lead labels 40, 41 can be formed from titanium, tantalum, tungsten, stainless steels, Nitinol, cobalt-chrome alloys, palladium, platinum, and other noble metals. The biocompatible metal substrate can be anodized to include an identifier. The identifier can include at least one of color and text. The header and lead labels 40 and 41 that include the identifier (e.g., at least one of color and text) can assist in the manufacture, assembly, and implanting of the IMD 12.

Figure 2:
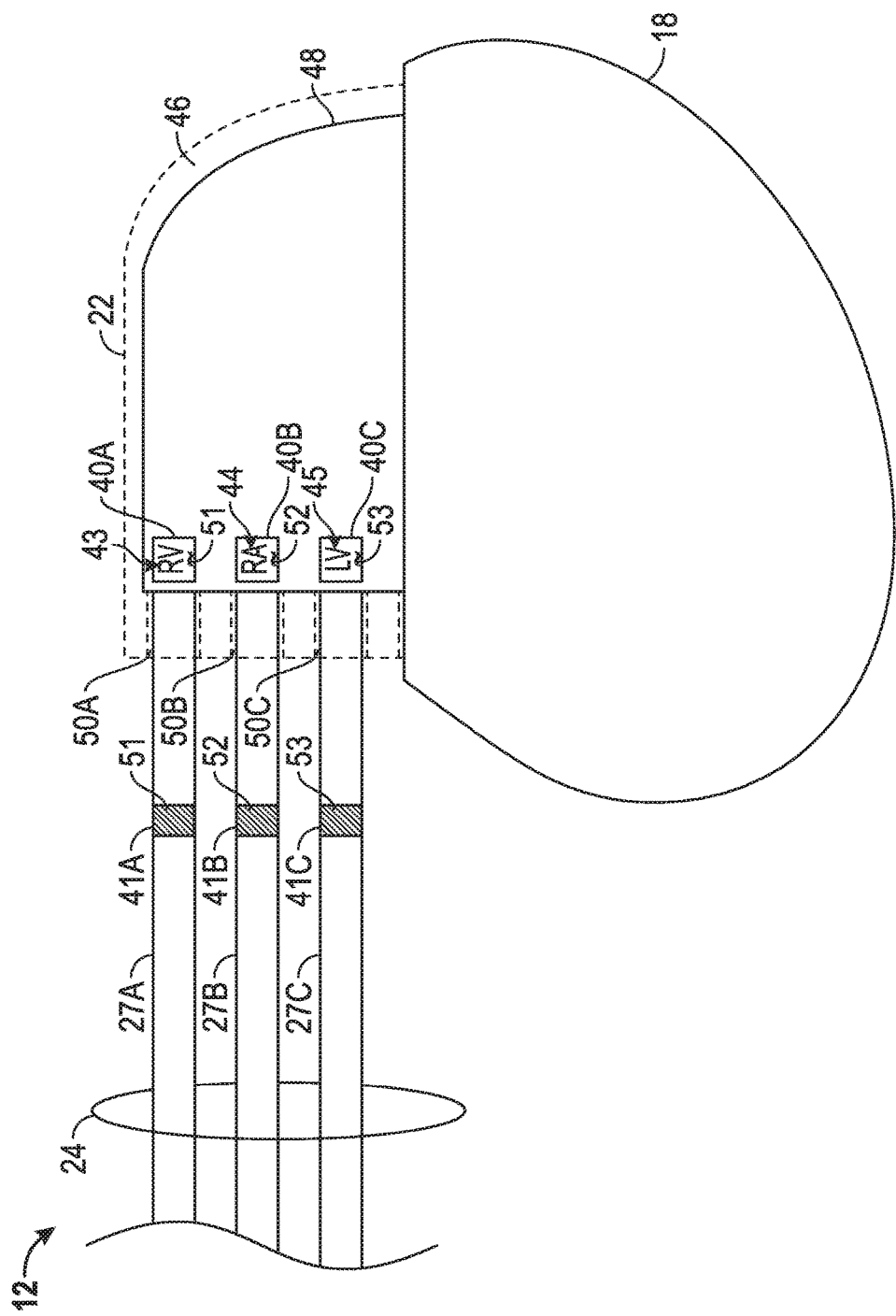
FIG. 2 illustrates generally a close-up of a portion of the example of the IMD of FIG. 1.

FIG. 2 illustrates generally an example of the IMD 12 of FIG. 1. The IMD 12 includes the housing 18, the header 22, and the lead assembly 24. In an example, the header 22 can include a core 48 positioned within a header housing 46. The header housing 46 and core 48 can define bores 50A-C (collectively referred to as "bores 50"). As illustrated in FIG. 2, each lead 27A-C is positioned within a respective bore 50A-C. For example, lead 27A is positioned in bore 50A, lead 27B is positioned in bore 50B, and lead 27C is positioned in bore 50C. The header labels 40 and the lead labels 41 can provide a visual aide to reduce the risk of incorrectly coupling the leads 27 to the header 22.

In an example, core 48 can be formed from a dielectric material such as polyurethane, polyether ether ketone, epoxy, and other materials. In an example, the header housing 46 can be translucent and formed form a dielectric material. The header housing 26 can be translucent such that the header labels 40 are visible through the header housing 46.

In an example, each of the header labels 40A-C can be anodized to provide an anodized metal label that includes an identifier. Anodizing can include growing an oxide layer on a surface, which can generate a range of different colors. A further explanation of anodizing is provided herein. Each identifier of the header labels 40A-C can substantially match an identifier of a respective header label of the header labels 40. Each header label 40A-C can be positioned adjacent to a respective bore of bores 50A-C to visually indicate a relationship with the particular bore. In an example, the header label 40A can be associated with the bore 50A. The header label 40A is associated with the bore 50A by being positioned on the core 48 at a location adjacent to the bore 50A to indicate the relationship. In an example, the header label 40B can be associated with the bore 50B and the header label 40C can be associated with the bore 50C.

As illustrated in the example of FIG. 2, the lead 27A, configured to connect to the housing 18 via the bore 50A, can include the lead label 40A having an identifier that substantially matches the identifier of the header label 40A, thereby indicating that the lead 27A is correctly coupled to the housing 18 via bore 50A. In an example, the identifier for the header label 40A and lead label 41A can be a color. That is, the surface of the header label 40A and the surface of the lead label 41A can be anodized to provide color 51. In an example, color 51 can be red. Therefore, an operator can easily and visually understand that the lead 27A (e.g., having color 51) connects to the housing 18 via bore 50A (e.g., having color 51) of the core 48.

In an example, the header label 40B can be associated with the bore 50B. Lead 27B can be configured to connect to the housing 18 via the bore 50B. The header label 40B and the lead label 41B can include the same identifier. For example, the surface of the header label 40B and the surface of the lead label 41B can be anodized to provide color 52. In an example, color 52 is different from color 51. In an example, color 51 can be red and color 52 can be blue. Therefore, an operator can easily and visually understand that the lead 27B (e.g., having color 52) connects to the housing 18 via bore 50B (e.g., having color 52).

In an example, the header label 40C can be associated with the bore 50C. Lead 27C can be configured to connect to the housing 18 via the bore 50C. The header label 40C and the lead label 41C can include the same identifier. For example, the surface of the header label 40 C and the surface of the lead label 41C can be anodized to provide color 53. In an example, color 53 is different from color 51 and color 52. For example, color 51 can be red, color 52 can be blue, and color 53 can be yellow. Therefore, an operator can easily and visually understand that the lead 27C (e.g., having color 53) connects to the housing 18 via bore 50C (e.g., having color 53).

Various biocompatible metals can be used to provide the header labels 40 and the lead labels 41. As discussed herein, anodizing biocompatible metals can provide a range of colors. For example, biocompatible metals can be anodized to provide colors including, but not limited to, black, grey, brown, purple, blue, yellow, red, orange, and green.

In an example, the header labels 40 can be anodized to provide text that can further help reduce the risk of incorrect assembly, manufacture, and implanting the IMD 12. The text can be provided to header labels 40 after the header labels 40 have been anodized to include a color (e.g., a background color). As illustrated in the example of FIG. 2, header label 40A can be anodized to provide text such as "RV" 43. As discussed in FIG. 1, lead 27A can be configured to be associated with the right ventricle of the heart 26. Thus, the text "RV" 43 can assist a surgeon while implanting the IMD 12. The text "RV" 43 can be black to contrast with the color 51 of the header label 40A. Header label 40B can include text "RA" 44 indicating the lead 27B is configured to be inserted into the right atrium. Further, header label 40C can include text "LV" 45 indicating the lead 27C is configured to be inserted into the left ventricle. In an example, the lead labels 41A-C can also be modified to include the text. In an example, the text can include letters, numbers, symbols, and/or other graphics.

Anodizing the biocompatible metal substrates to provide color and text can be done by at least one of an electrochemical anodizing process and a LASER anodizing process. In an example, the color can be provided by using the electrochemical anodizing process and the text can be provided by using the LASER anodizing process. The electrochemical anodizing process can include electrochemically growing an oxide layer on the surface of the biocompatible metal substrate to form the header and lead labels 40, 41 including a first identifier (e.g., color). For example, voltage can be applied to an electrolytic bath including the component to include the color. The voltage applied can control the thickness of the oxide layer, which determines the color produced on the component.

The LASER anodizing process can include growing oxide layers on the surface of the biocompatible metal substrate via a laser treatment. For example, oxide layers are grown to precise thicknesses based on laser heating in an oxygen bearing atmosphere. In an example, either the electrochemical or the LASER anodizing process can be used to provide the color. In an example, the electrochemical anodizing process can be used to provide the color and the LASER anodizing process can be used to provide the text.

In the example of FIG. 2, the header labels 40A-C have a square shape. However, the shapes of the header labels 40A-C can include other shapes. For example, the shapes of the header labels 40A-C can be modified to be different from each other to further distinguish the header labels 40A-C from each other. In an example, header label 40A can be a square, header label 40B can be a triangle, and header label 40C can be a circle.

Figure 3A:
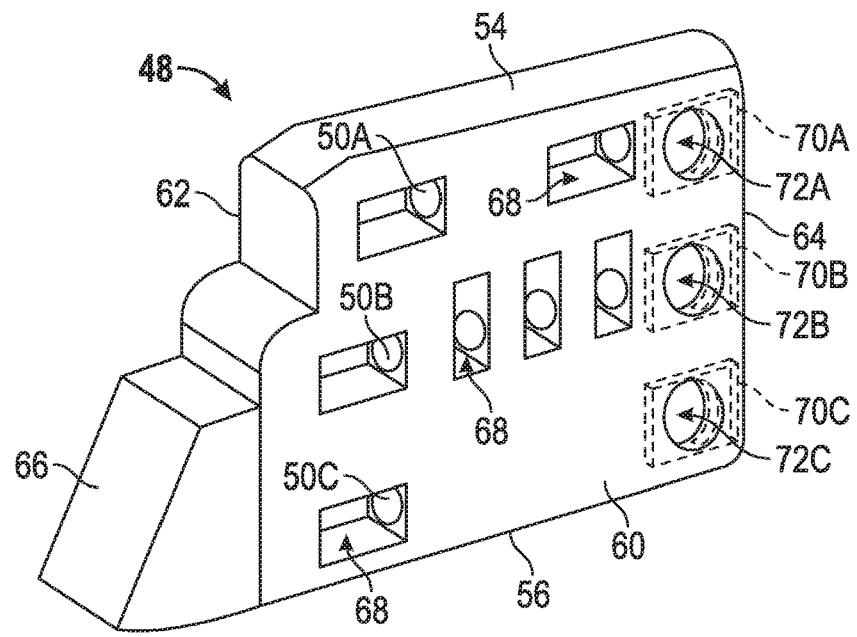
FIG. 3A is a perspective view of the example of a core of the IMD of FIG. 2.

FIG. 3A is a perspective view of an example of the core 48 of the IMD 12 of FIG. 2. The core 48 can include a superior surface 54, an inferior surface 56, and two side wall surfaces 64, 66. A first face 60 and a second face 62 can extend between the superior surface 54, the inferior surface 56, and the two side wall surfaces 64, 66. The core 48 can include the bores 50A-C extending from the first side wall surface 64 toward the second side wall surface 66. The core 48 can include a plurality of connector block openings 68 configured to receive connector blocks (as shown as connector blocks 104A-B, 106A-D, and 108 in FIG. 7). The connector block openings 68 can extend from the first face 60 to the second face 62 of the core 48. In another example, one or more of the plurality of connector block openings 68 extend partially into the core 48. The connector block openings 68 can be in communication with the bores 50A-C such that the connector blocks, when inserted into the connector block openings 68, interface with contact surfaces of the leads 27A-C.

In the example of FIG. 3A, the core 48 includes receiving cavities 70A-C along the first side wall 64 of the core 48. The receiving cavities 70A-C can be slots that extend into the first side wall 64 of the core 48 and are configured to receive the header labels 40A-C. For example, the header labels 40A-C can be metal substrates that are sized and shaped to be inserted into the receiving cavities 70A-C. The core 48 can include windows 72A-C that are in communication with the receiving cavities 70A-C. For example, when the header labels 40A-C are inserted into the receiving cavities 70A-C, a portion of the surface of the header labels 40A-C is visible through the windows 72A-C. The receiving cavities 70A-C can have a larger area than the windows 72A-C to provide initial stability when the metal substrates (e.g., pre-anodized or blank) are inserted into the receiving cavities 70A-C. As discussed herein, the header labels 40A-C can be anodized prior to being inserted into the receiving cavities 70A-C or after being inserted into the receiving cavities 70A-C. In one example, the header labels 40A-C can be anodized prior to being inserted into the receiving cavities 70A-C, and the text (as discussed herein with FIG. 2) can be provided to the header labels 40A-C after the header labels 40A-C are inserted into the receiving cavities 70A-C.

Figure 3B:
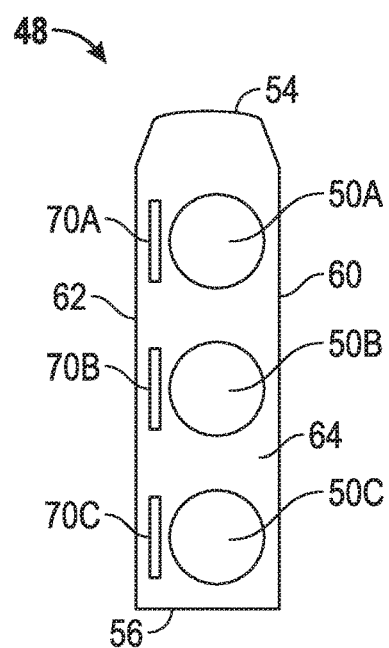
FIG. 3B is a side view of the example of the core in FIG. 3A.

FIG. 3B is a side view of the example of the core 48 in FIG. 3A. In the example shown in FIG. 3B, the receiving cavities 70A-C are positioned adjacent to the bores 50A-C. For example, receiving cavity 70A is positioned adjacent to bore 50A, receiving cavity 70B is positioned adjacent to bore 50B, and receiving cavity 70C is positioned adjacent to bore 50C. In other words, receiving cavity 70A is positioned closer to bore 50A than bore 50B or 50C, receiving cavity 70B is positioned closer to bore 50B than bore 50A or 50C, and receiving cavity 70C is positioned closer to bore 50C than bore 50A or 50B.

Figure 4:
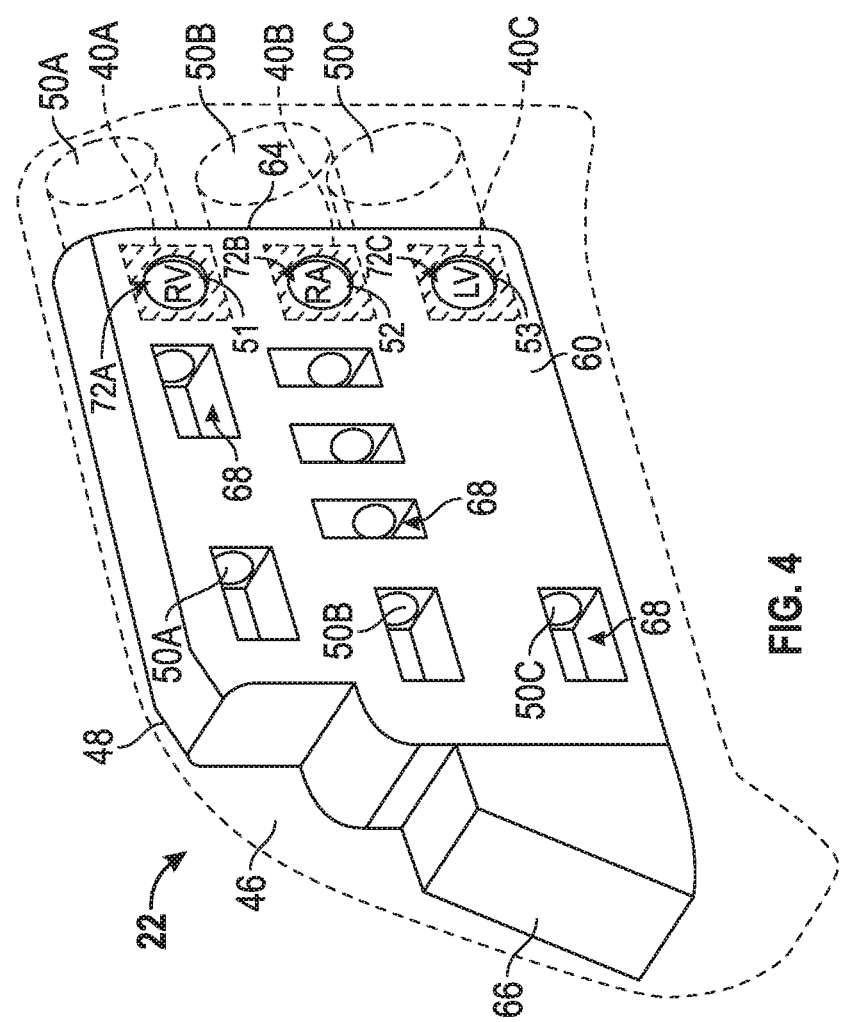
FIG. 4 is a perspective view of an example of a header including the core in FIG. 3A.

FIG. 4 is a perspective view of an example of a header 22 of the IMD 12. The header 22 can include the core 48 (as shown in FIGS. 3A and 3B) and the header housing 46. The header housing 46 can be overmolded over the core 48. The header housing 46 and the core 48 can define the bores 50A-C that can be configured to receive the leads 27A-C (shown in FIGS. 1 and 2). In the example of FIG. 4, the header labels 40A-C are positioned within the receiving cavities (shown as 70A-C in FIG. 3B). In an example, the header labels 40A-C are square metal substrates that have a surface area greater than the area of the windows 72A-C. Providing the header labels 40A-C with a surface area greater than the windows 72A-C can allow for the header labels 40A-C to be securely positioned within the core prior to anodizing (e.g., for color and/or text) and/or overmolding.

In one example, the header labels 40A-C can be inserted into the receiving cavities 70A-C as blank metal substrates and can be anodized (e.g., to include color and text) after being inserted into the core 48. In another example, the header labels 40A-C can be anodized (e.g., to include color and text) prior being inserted into the receiving cavities 70A-C.

In an example, the header labels 40A-C can be anodized to provide a first identifier (e.g., color) prior to being inserted into the receiving cavities 70A-C and can be anodized to provide a second identifier (e.g., text) after being inserted into the receiving cavities 70A-C. For example, header label 40A can be anodized to include color 51, header label 40B can be anodized to include color 52, and header label 40C can be anodized to include color 53. After the color is added to each of the header labels 40A-C, the header labels 40A-C can be inserted into the receiving cavities 70A-C. In an example where text is to be provided, the text can be provided to the header labels 40A-C after the header labels 40A-C have been inserted into the receiving cavities 70A-C. For example, the header labels 40A-C can be anodized to include the text. For example, the text "RA", "LV" and "RV" can be provided to header labels 40A-C after the header labels 40A-C have been inserted into the receiving cavities 70A-C. In that way, the text can be sure to be visible through the windows 72A-C. In an example, the first identifier (e.g., color) is added to the header labels 40A-C prior to the second identifier (e.g., text).

In an example, the header labels 40A-C can have a size that is greater than the windows 72A-C and the header labels 40A-C are inserted into the receiving cavities. In an example, the windows 72A-C can be the receiving cavities and the header labels 40A-C can be placed into the windows 72A-C. For example, the header labels 40A-C can have substantially the same as the windows 72A-C such that header labels 40A-C can be placed into the windows 72A-C acting as the receiving cavity. In another example, the core 48 does not include receiving cavities and the header labels 40A-C are coupled to the first face 60 of the core 48, for example, via a biocompatible adhesive.

Figure 5A:
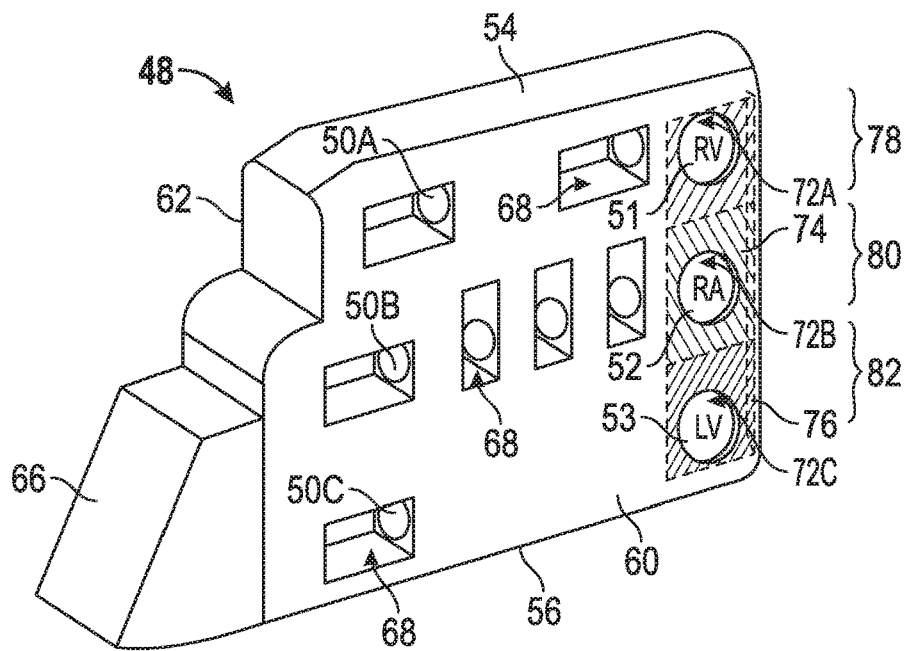
FIG. 5A is a perspective view of an example of a core of the IMD of FIG. 2.
Figure 5B:
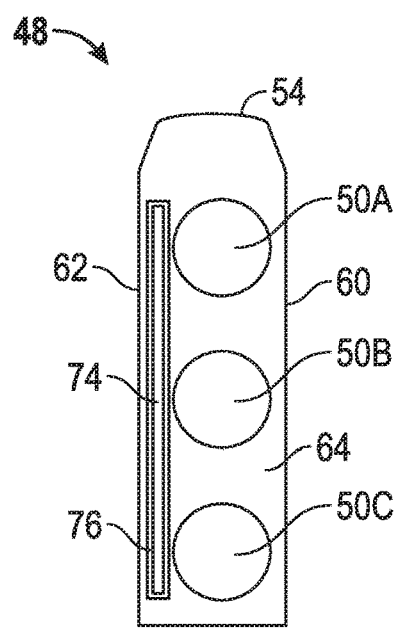
FIG. 5B is a side view of the example of the core in FIG. 5A.

FIG. 5A is a perspective view of an example of the core 48 of the IMD of FIG. 2. While the header labels 40A-C in FIG. 4 are illustrated as separate independent labels, FIG. 5A illustrates an example of a core 48 including a single header label 74. For example, the core 48 can include a single receiving cavity 76 (as shown in FIG. 5B) along the first side wall 64. The header label 74 can be inserted into the receiving cavity 76 such that portions of the header label 74 can be seen through the windows 72A-C. The header label 74 can be selectively anodized such that a portion 78 of the header label 74 adjacent to the bore 50A has the color 51, a portion 80 of the header label 74 adjacent to the bore 50B has the color 52, and a portion 82 of the header label 74 adjacent to the bore 50C has the color 53. In an example, the portions 78, 80, and 82 can also be anodized to include text. For example, portion 78 can include text "RV," portion 80 can include text "RA," and portion 82 can include text "LV."

Figure 6:
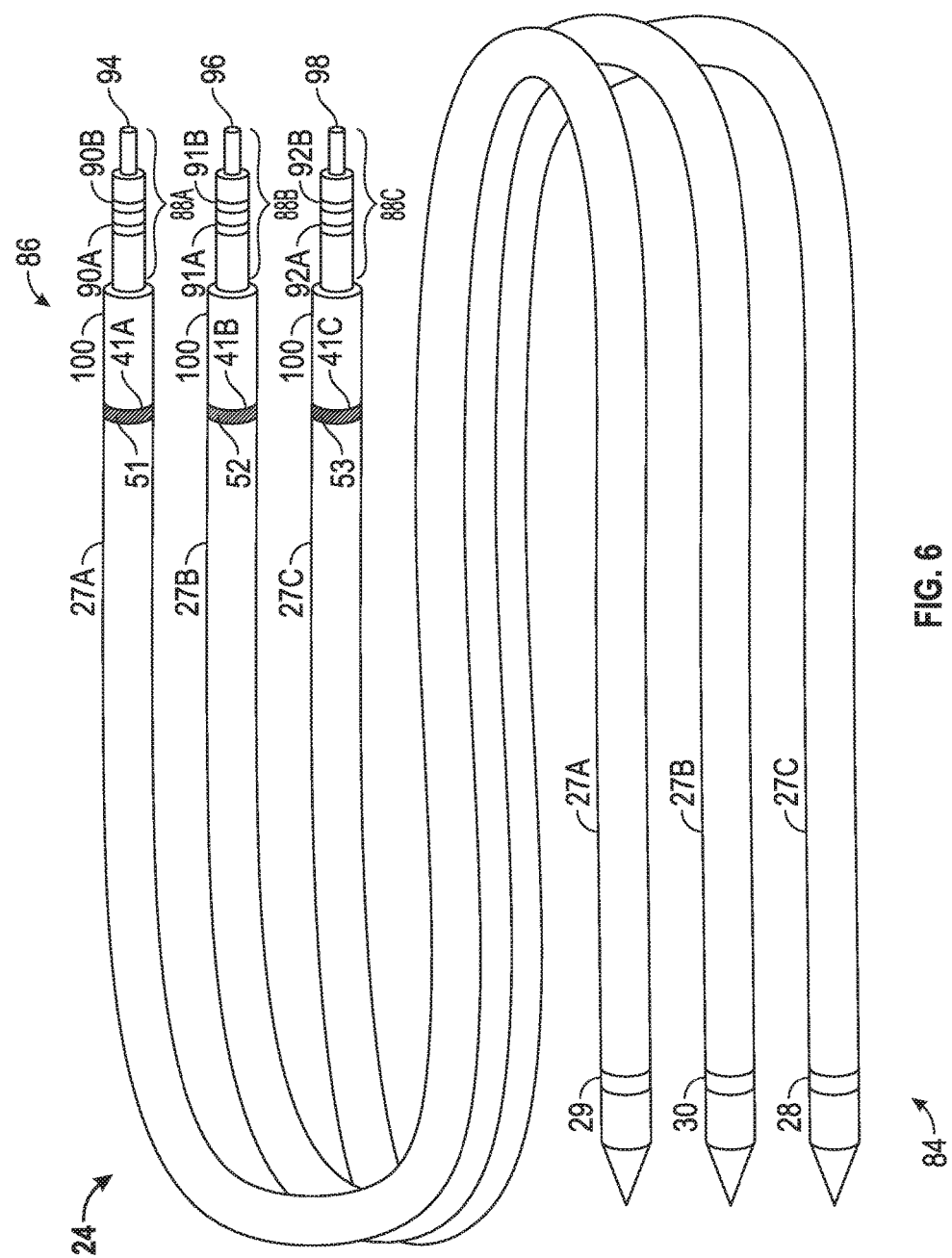
FIG. 6 is a perspective view of an example of a lead assembly of the IMD 12.

FIG. 6 is a perspective view of an example of a lead assembly 24 of the IMD 12. As discussed herein, the IMD 12 can include one or more lead assemblies such as lead assembly 24. The lead assembly 24 can include the leads 27A-C. The leads 27A-C can include a distal end 84 and a proximal end 86. The distal end 84 can include electrodes configured to provide therapy to adjacent tissue. For example, lead 27A can include electrode 29, lead 27B can include electrode 30, and lead 27C can include lead 29. In an example, the proximal end 86 can include lead labels 41A-C, as discussed herein.

The lead labels 41A-C can be formed from biocompatible materials. For example, the lead labels 41A-C can be formed from biocompatible metals such as titanium, tantalum, tungsten, stainless steels, Nitinol, cobalt-chrome alloys, palladium, platinum, and other noble metals. Each of lead labels 41A-C can include an identifier. For example, the identifier can include at least one of a color and text. In the example of FIG. 4, lead label 41A can be anodized to have the color 51, lead label 41B can be anodized to have the color 52, and lead label 41C can be anodized to have the color 53.

In an example, the lead labels 41A-C can be annular rings that are positioned around an exterior surface 100 of leads 27A-C. In an example, the lead labels 41A-C can have an interference fit with the leads 27A-C. For example, the lead labels can be crimped onto the leads 27A-C. The portion of the leads 27A-C that include the lead labels 41A-C positioned around the exterior surface can be overmolded with a transparent polymeric material to provide a smooth exterior surface 100, while allowing the identifier (e.g., color or text) to be visible.

In an example, the lead labels 41A-C can be integrated into a body of the leads 27A-C. For example, annular metal rings can be anodized and can be molded into the body of the leads with transparent polymeric materials.

The proximal end 86 of leads 27A-C can include a proximal portion 88A-C that is configured to be received within the bores 50A-C of header 22 (as shown in FIG. 2). The proximal portions 88A-C can include contact surfaces configured to contact connector blocks within the core, as discussed herein, and a tip. For example, lead 27A can include portion 88A that is configured to be received within bore 50A (shown in FIG. 2). Portion 88A can include a tip contact 94 and contact rings 90A and 90B. Lead 27B can include portion 88B that is configured to be received within bore 50B (shown in FIG. 2). Portion 88B can include a tip contact 96 and contact rings 91A and 91B. Lead 27C can include portion 88C that is configured to be received within bore 50C (shown in FIG. 2). Portion 88C can include a tip contact 98 and contact rings 92A and 92B. While portions 88A-C each include two contact rings and one tip contact, other configurations are possible. For example, each portions 88A-C can include one to three ring contacts and one tip contact.

The tip contacts 94, 96, and 98 and the contact rings 90A, 90B, 91A, 91B, 92A, and 92B can be formed from biocompatible materials as discussed herein. In some examples, the tip contacts 94, 96, and 98 and/or one or more of the contact rings 90A, 90B, 91A, 91B, 92A, and 92B can be anodized to provide the identifier. In an example, the tip contacts can be anodized to provide the identifier. That is the tips 94, 96, and 98 and/or one or more of the contact rings 90A, 90B, 91A, 91B, 92A, and 92B can be the lead labels for the leads 27A-C. For example, the tip contact 94 and/or one or more of contact rings 90A and 90B can be anodized to provide the color 51, the tip contact 96 and/or one or more of contact surfaces 91A and 91B can be anodized to provide the color 52, and tip contact 98 and/or one or more contact surfaces 92A and 92B can be anodized to provide the color 53.

Figure 7:
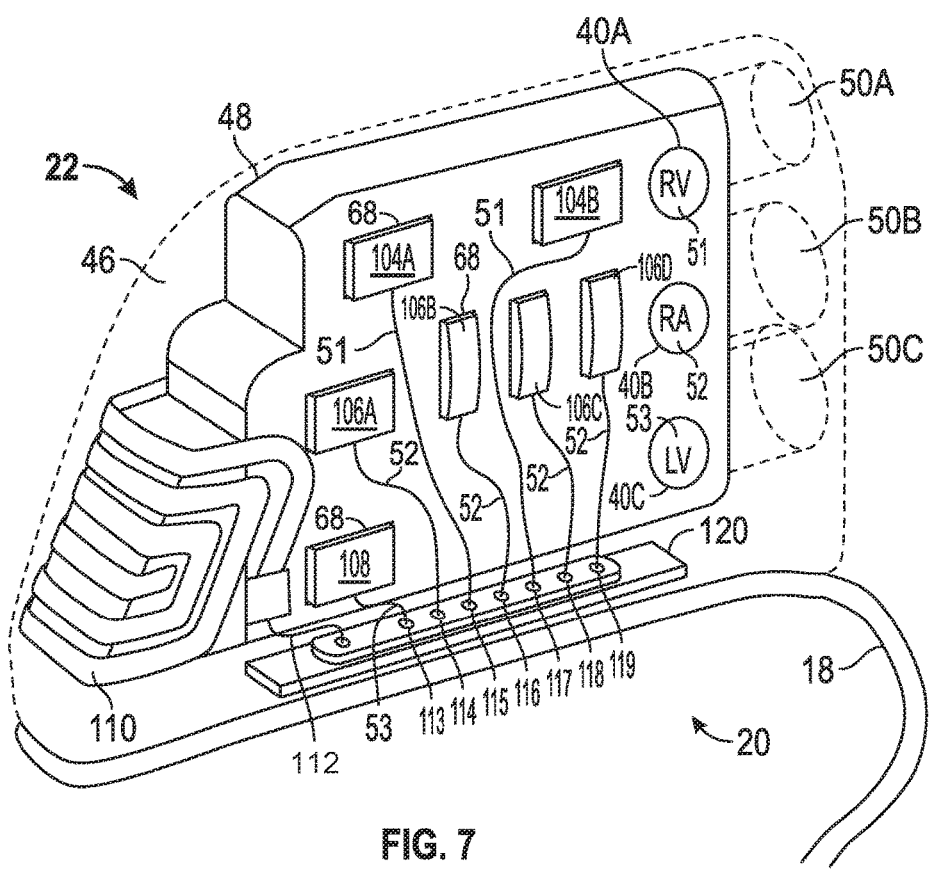
FIG. 7 is a perspective view of an example of a header and housing of the IMD 12.

FIG. 7 is a perspective view of an example of a header 22 and a housing 18 of the IMD 12. As discussed herein, header 22 can include a core 48 positioned within the header housing 46, where the header housing 46 and the core 48 define bores 50A-C. In the example of FIG. 7, the header 22 can include an antenna 110 positioned along a portion of the core 48 and at least partially within the header housing 46.

The header 22 in FIG. 7 includes connector blocks 104A-B, 106A-D, and 108 positioned within the connector block openings 68. Connector blocks 104A-B, 106A-D, and 108 can electrically and mechanically mate with one or more of the leads 27A-C. For example, the connector blocks 104A-B, 106A-D, and 108 can provide contact surfaces that can interact with the contact rings 90A, 90B, 91A, 91B, 92A, and 92B and tip contacts 94, 96, and 98 of the leads 27A-C (as shown in FIG. 6) when the leads 27A-C are positioned within the bores 50A-C.

In an example, a plurality of contact wires 112, 113, 114, 115, 116, 117, 118, and 119 can extend from a top portion 120 of the housing 18. The contact wires 112, 113, 114, 115, 116, 117, 118, and 119 can couple with the connector blocks 104A-B, 106A-D, and 108 to electrically couple the leads 27A-C to the electrical circuitry 20 contained within the housing 18. While the example of FIG. 7 includes eight contact wires, the number of contact wires can depend on the type of IMD 12 and the therapy to be provided. In one example, the number of contact wires can vary between 2 wires to 32 wires. In an example, the number of contact wire can be greater than 32 wires. However, as the number of contact wires increases, the risk of incorrectly connecting wires (e.g., wire crossing) can also increase.

In an example, one or more of the contact wires 112, 113, 114, 115, 116, 117, 118, and 119 can be anodized to include an identifier such as a color. For example, contact wires 115 and 117 are configured to couple to connector blocks 104A and 104B associated with bore 50A. Thus, contact wires 115 and 117 can be anodized to include an identifier such as the color 51 (e.g., red). Thus, an operator can easily and visually confirm that contact wires 115 and 117 (having color 51) are to be coupled to the connector blocks 104A-B associated with bore 50A (having header label 40A including color 51).

In an example, contact wires 114, 116, 118, and 119 can be anodized to include an identifier such as the color 52 (e.g., blue). Thus, an operator can easily and visually confirm that contact wires 114, 116, 118, and 119 (having color 52) are to be coupled to the connector blocks 106A-D associated with bore 50BA (having header label 40B including color 52). Further, contact wire 113 can be anodized to include an identifier such as the color 53 (e.g., yellow). Thus, an operator can easily and visually confirm that contact wire 113 (having color 53) is to be coupled to the connector block 108 associated with bore 50C (having header label 40C including color 53). The contact wire 112 may not be anodized and have a color of a pre-anodized biocompatible metal (e.g., silver).

In an example, connector blocks 104A-B, 106A-D, and 108 can also be anodized to include the identifier (e.g., color) to further assist the operator or surgeon. For example, connector blocks 104A-B can be anodized to have color 51, connector blocks 106A-D can be anodized to have color 52, and connector block 108 can be anodized to include color 53. The connector blocks can be anodized in addition to or in lieu of the header labels 40A-C. In one example, the header labels 40A-C can only include the text "RV", "RA", and "LV", respectively, while the connector blocks can include colors 51, 52, and 52, respectively.

Figure 8:
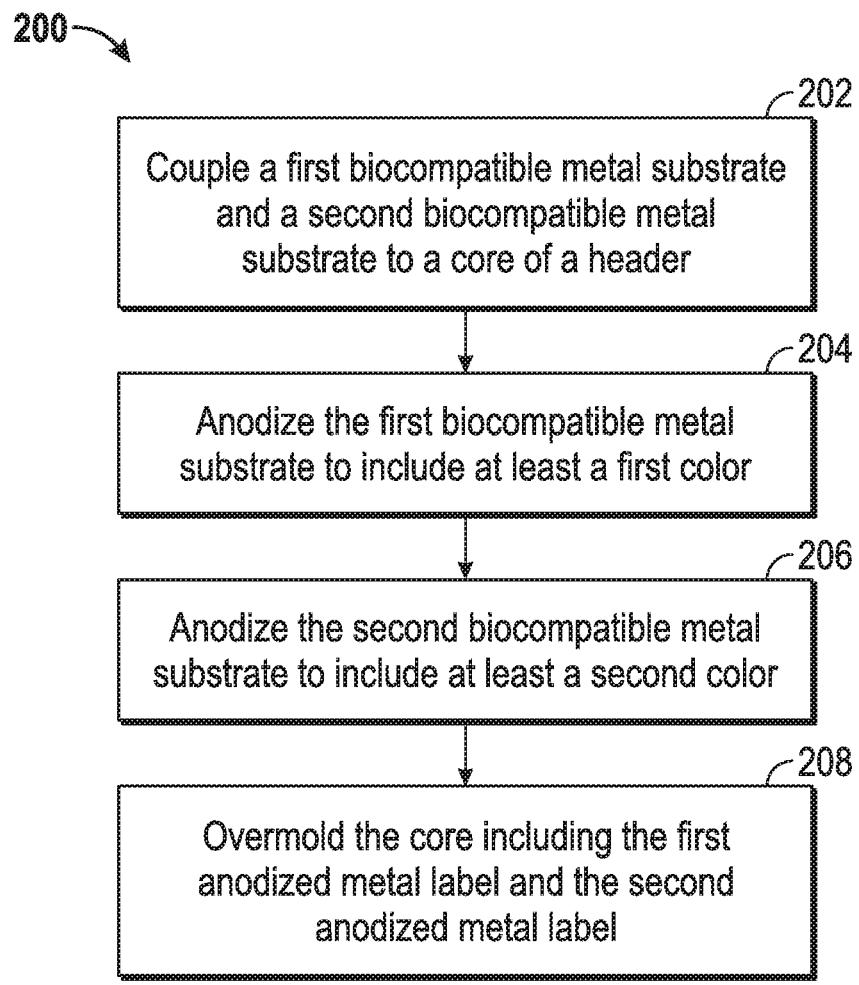
FIG. 8 illustrates generally an example of a method of labeling an implantable medical device.

FIG. 8 is an example of a method 200 of labeling an IMD. In describing the method 200 reference is made to features and elements previously described herein, including numbered references. Numbered elements provided within the description of the method 200 are not intended to be limiting, instead numbered references are provided for convenience and can include any similar features described herein, as well as their equivalents.

The method 200, at 202, can include coupling a first biocompatible metal substrate and a second biocompatible metal substrate to a core of a header of the implantable medical device. For example, a first biocompatible metal substrate and a second biocompatible metal substrate can be coupled to a core 48 of a header 22 of the IMD 12. The core 48 can have a first bore 50A and a second bore 50B, where the first biocompatible metal substrate is positioned adjacent to the first bore 50A and the second biocompatible metal substrate is positioned adjacent to the second bore 50B. For example, the metal substrates can be the header labels 40A and 40B, as shown in FIG. 4. Coupling the biocompatible metal substrates can be done as described herein with reference to FIGS. 3A and 3B. For example, the biocompatible metal substrates (e.g., header labels 40A and 40B) can be inserted into receiving cavities 70A and 70B.

The method 200 can include forming the core 48 to include a first receiving cavity (e.g., receiving cavity 70A) and a second receiving cavity (e.g. receiving cavity 70B). The first receiving cavity 70A can be configured to receive the first biocompatible metal substrate (e.g., header label 40A) and the second receiving cavity can be configured to receive the second biocompatible metal substrate (e.g., header label 40B).

Method 200, at 204, can include anodizing the first biocompatible metal substrate to include at least a first color and, at 206, method 200 can include anodizing the second biocompatible metal substrate to include at least a second color. As discussed herein, the first color and second color are different from each other. In one example, the electrochemical anodizing process can be used. In another example, the first and second color can be provided using the LASER anodizing process.

The method 200 can include anodizing the first biocompatible metal substrate to include a first text and anodizing the second biocompatible metal substrate to include a second text, where the second text is different from the first text. For example, as shown in FIG. 4, the header label 40A can be anodized to include the text "RV." In one example, the LASER anodizing process can be used to provide the text. In an example, the text can be provided in a color such as black thereby to contrast with the first and second colors provided to the first and second biocompatible metal substrates, respectively.

Anodizing can generate an array of different colors without using dyes or inks. The anodizing process provides an oxidized surface with controlled thicknesses on the scale of visible light wavelengths. The color formed is dependent on the thickness of the oxide layer, which is determined by a variety of process factors. During the electrochemical anodizing process, voltage is applied to an electrolytic bath including the component to include the color. The voltage applied can control the thickness of the oxide layer and thereby control the color produced on the component. During the LASER anodizing process, a laser beam is passed over the surface of the metal substrate. The pulse rate, power (e.g., voltage), focal point size, rate traveled, and pass rate of the laser, component mass, thermal conductivity, process atmosphere, thermal fixtures, focal depth, and angles of incidence can affect the thickness of the oxide layer and thereby control the color produced on the component.

The method 200 can include texturing the surface of the biocompatible metal substrates prior to or after anodizing the biocompatible metal substrates. The textured surface can minimize refraction such that an average color is represented to the viewer. The textured surface can provide a more constant and accurate color that is not dependent on a viewing angle. In one example, the biocompatible material, prior to or after anodizing, can be sent through a press having protrusions to provide a textured surface. In another example, the laser beam used to provide the anodizing can be utilized to texture the surface.

As discussed herein, the method 200 can include anodizing the first biocompatible metal substrate and anodizing the second biocompatible metal substrate prior to coupling the first biocompatible metal substrate and the second biocompatible metal substrate to the core. Alternatively, the method 200 can include anodizing the first biocompatible metal and anodizing the second biocompatible metal substrate after coupling the first biocompatible metal substrate and the second biocompatible metal substrate to the core.

In one example, the biocompatible metal substrates are anodized using the electrochemical anodizing process to provide the color. The anodized biocompatible metal substrates can then be coupled to core of the header. Once coupled to the core, the biocompatible metal substrates can be anodized using the LASER anodizing process to provide the text.

The method 200, at 208, can include overmolding the core including the first biocompatible metal substrate and the second biocompatible metal substrate. For example, core 48 including the biocompatible metal substrates (e.g., header labels 40A-40C) can be overmolded to form the header housing 46 of the header 22. That is the header housing 46 can be overmolded or otherwise formed around the core 48.

The method 200 can include coupling a first lead of a lead assembly to the first bore and coupling a second lead of a lead assembly to the second bore. For example, lead 27A of lead assembly 24 can be coupled to bore 50A and lead 27B of lead assembly 24 can be coupled to bore 50B.

The method 200 can include anodizing a first annular ring to include the first color and anodizing a second annular ring to include the second color. For example, the first annular ring 41A can be anodized to form a color (e.g., color 51), which is the same as the color 51 of the header label 40A. Additionally, the second annular ring 41B can be anodized to form a color (e.g., color 52), which is the same as the color 52 of the header label 40B. The method 200 can include coupling the first annular ring to a proximal end of the first lead 27A and coupling the second annular ring 41B to a proximal end of the second lead 27B. For example, the annular rings 41A-C can be coupled to the leads 27A-C by an interference fit and crimping. Additionally, the annular rings 41A-C can be positioned within a circumferential groove of the leads 27A-C. In an example, the lead labels 41A-C can be integrated into a body of the leads 27A-C. For example, annular metal rings (e.g., lead labels 41A-C) can be anodized and can be molded into the body of the leads 27A-C with transparent polymeric materials.

The method 200 can include anodizing a first contact wire extending from a housing including electronic circuitry to include the first color and anodizing a second contact wire extending from the housing to include the second color. As described herein with respect to the example of FIG. 7, contact wires 112-119 can be anodized to include a color. The color of each of the contact wires 112-119 can assist a user in connecting the contact wires 112-119 to the header 22. For example, contact wires 115 and 117 are configured to couple to connector blocks 104A and 104B associated with bore 50A. Thus, contact wires 115 and 117 can be anodized to include an identifier such as the color 51 (e.g., red). Contact wires 114, 116, 118, and 119 can be anodized to include an identifier such as the color 52 (e.g., blue). Further, contact wire 113 can be anodized to include an identifier such as the color 53 (e.g., yellow).

The method 200 can include coupling the first contact wire to the connector block positioned within the first bore and coupling the second contact wire to a connector block positioned within the second bore. For example, contact wires 115 and 117 (e.g., having color 51) can be coupled to the connector blocks 104A-B associated with bore 50A (e.g., having header label 40A including color 51), contact wires 114, 116, 118, and 119 (e.g., having color 52) can be coupled to the connector blocks 106A-D associated with bore 50BA (e.g., having header label 40B including color 52), and contact wire 113 (e.g., having color 53) can be coupled to the connector block 108 associated with bore 50C (e.g., having header label 40C including color 53).

Figure 9:
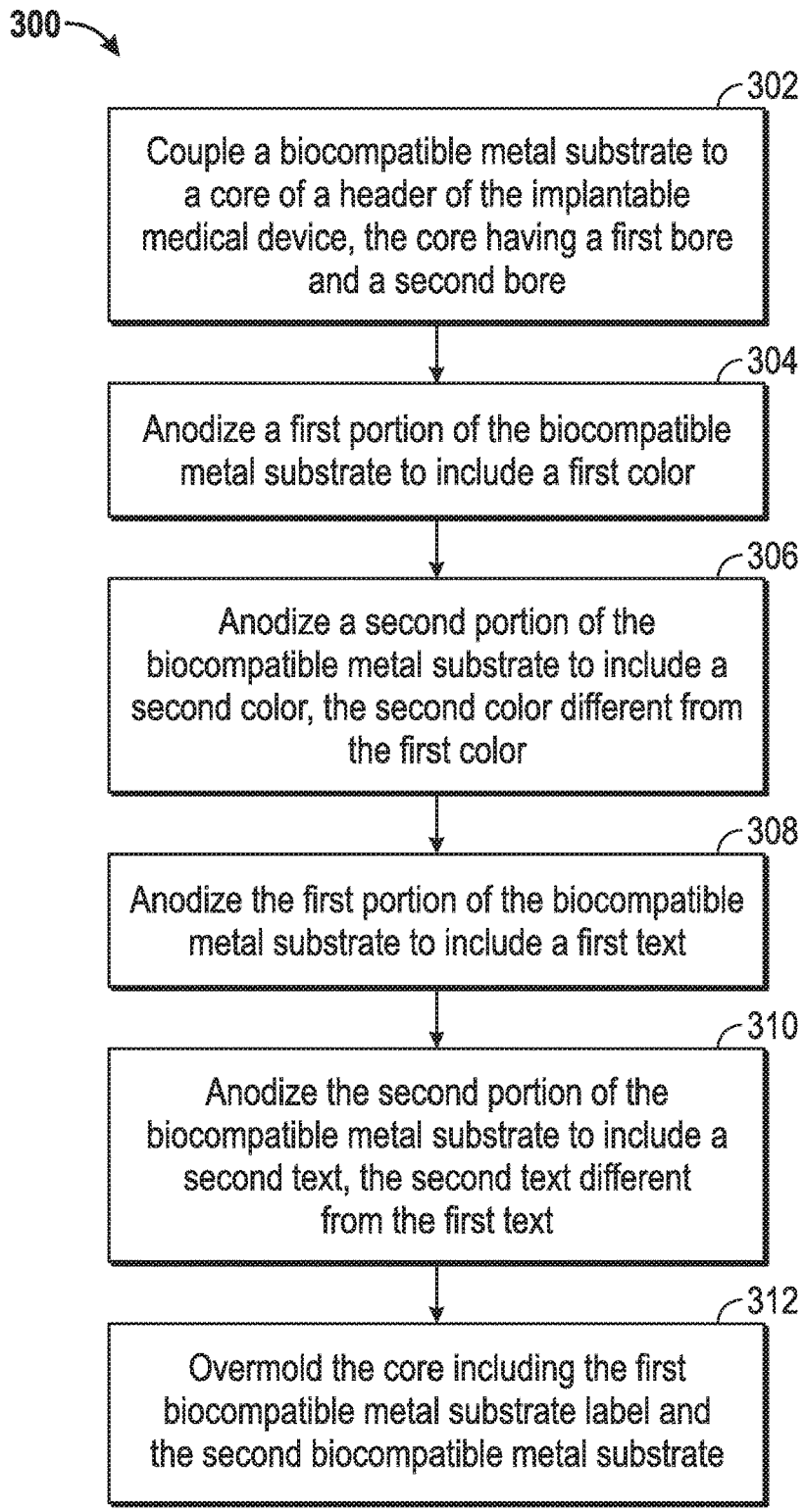
FIG. 9 illustrates generally an example of a method of labeling an implantable medical device.

FIG. 9 is an example of a method 300 of labeling an IMD. In describing the method 300 reference is made to features and elements previously described herein, including numbered references. Numbered elements provided within the description of the method 300 are not intended to be limiting, instead numbered references are provided for convenience and can include any similar features described herein, as well as their equivalents.

The method 300, at 302, can include coupling a first biocompatible metal substrate to a core of a header of the implantable medical device. For example, a biocompatible metal substrate (e.g., header label 74) can be coupled to a core 48, as shown in FIG. 5A. The core 48 can have a first bore 50A and a second bore 50B. Coupling the biocompatible metal substrate to the core can be done as described herein with reference to FIGS. 5A and 5B. For example, the biocompatible metal substrate (e.g., header label 74) can be inserted into receiving cavity 76. Method 300 can include forming the core 48 to include the receiving cavity 76, where the first receiving cavity 76 can be configured to receive the biocompatible metal substrate (e.g., header label 76).

Method 300, at 304, can include anodizing a first portion of the biocompatible metal substrate to include a first color, and at 306 can include anodizing a second portion of the biocompatible metal substrate to include a second color. For example, the header label 74 can be selectively anodized such that a portion 78 of the header label 74 adjacent to the bore 50A has the color 51, a portion 80 of the header label 74 adjacent to the bore 50B has the color 52, and a portion 82 of the header label 74 adjacent to the bore 50C has the color 53.

As discussed herein, the method 300 can include anodizing the first portion of the biocompatible metal substrate and anodizing the second portion of the biocompatible metal substrate prior to coupling the biocompatible metal substrate to the core. In one example, the first and second portion of the biocompatible metal substrate can be anodized using the electrochemical anodizing process to provide the color.

Optionally, method 300, at 308, can include anodizing the first portion of the biocompatible metal substrate to include a first text, and at 310, can include anodizing the second portion of the biocompatible metal substrate to include a second text. The method 300 can include anodizing the first and second portion of the biocompatible metal substrate to include the first and second text, respectively, after coupling the biocompatible metal substrate to the core. In one example, the first and second portion of the biocompatible metal substrate can be anodized to provide text using the LASER anodizing process, as described herein.

The method 300, at 312, can include overmolding the core including the biocompatible metal substrate. For example, core 48 including the biocompatible metal substrate (e.g., header labels 74) can be overmolded to form the header housing of the header 22. That is the header housing can be overmolded or otherwise formed around the core 48, as described herein.

Additional Notes and Examples

Example 1 can include subject matter that can include an implantable medical device, comprising a housing including electronic circuitry, a header coupled to the housing and including a core, the core defining a bore and including a first metal label positioned adjacent to the at least one bore, and a lead assembly including at least one lead having a distal end and a proximal end, the at least one lead including a second metal label, the distal end including at least one electrode and the proximal end received within the bore.

Example 2 can include, or can optionally be combined with the subject matter of Example 1, to optionally include where the first metal label and the second metal label are chosen from at least one of titanium, tantalum, tungsten, and stainless steel.

Example 3 can include, or can optionally be combined with the subject matter of one or any combination of Examples 1 or 2, to optionally include where the first metal label includes a first identifier and the second metal label includes a second identifier, the first identifier substantially the same as the second identifier.

Example 4 can include, or can optionally be combined with the subject matter of one or any combination of Examples 1-3, to optionally include where the first identifier and the second identifier include at least one of a color and text.

Example 5 can include, or can optionally be combined with the subject matter of one or any combination of Examples 1-4, to optionally include where the first identifier is a first color and the second identifier is a second color, the second color and the first color being substantially the same.

Example 6 can include, or can optionally be combined with the subject matter of one or any combination of Examples 1-5, to optionally include where the first metal label is an anodized metal substrate.

Example 7 can include, or can optionally be combined with the subject matter of one or any combination of Examples 1-6, to optionally include where a surface of the anodized metal substrate is textured Example 8 can include, or can optionally be combined with the subject matter of one or any combination of Examples 1-7, to optionally include where a surface of the core defines a receiving cavity adjacent to the bore, the receiving cavity configured to receive the first metal label.

Example 9 can include, or can optionally be combined with the subject matter of one or any combination of Examples 1-8, to optionally include where the second metal label is an anodized metal annular ring.

Example 10 can include, or can optionally be combined with the subject matter of one or any combination of Examples 1-9, to optionally include where an exterior surface of the anodized metal annular ring is textured.

Example 11 can include, or can optionally be combined with the subject matter of one or any combination of Examples 1-10, to optionally include where an exterior surface of the lead defines a circumferential groove configured to receive the second metal label.

Example 12 can include, or can optionally be combined with the subject matter of one or any combination of Examples 1-11, to optionally include where the core is overmolded with a dielectric material.

Example 13 can include, or can optionally be combined with the subject matter of one or any combination of Examples 1-12, to optionally include where at least a portion of the lead having the second metal is overmolded with a dielectric material.

Example 14 can include subject matter that can include an implantable medical device, comprising a housing including electronic circuitry, wherein a first contact wire and a second contact wire extend from the housing, the first contact wire including a first identifier and the second contact wire including a second identifier, a header coupled to the housing, the header comprising a core defining a first bore and a second bore, a first connector block in communication with the first bore, a second connector block in communication with the second bore, a first anodized metal label positioned adjacent to the first bore, and a second anodized metal label positioned adjacent to the second bore, and a lead assembly including a first lead and a second lead, wherein the first lead is electrically coupled to the electronic circuitry via the first connector block and the second lead is electrically coupled to the electronic circuitry via the second connector.

Example 15 can include, or can optionally be combined with the subject matter of one or any combination of Examples 1-14, to optionally include where the first contact wire is anodized to provide the first identifier, the first identifier being a first color.

Example 16 can include, or can optionally be combined with the subject matter of one or any combination of Examples 1-15, to optionally include where the second contact wire is anodized to provide the second identifier, the second identifier being a second color different from the first color.

Example 17 can include, or can optionally be combined with the subject matter of one or any combination of Examples 1-16, to optionally include where the first anodized metal label includes the first color.

Example 18 can include, or can optionally be combined with the subject matter of one or any combination of Examples 1-17, to optionally include where the second anodized metal label includes the second color.

Example 19 can include, or can optionally be combined with the subject matter of one or any combination of Examples 1-18, to optionally include where the first connector block has been anodized to include the first color and the second connector block has been anodized to include the second color.

Example 20 can include, or can optionally be combined with the subject matter of one or any combination of Examples 1-19, to optionally include where the first anodized metal label and the second anodized metal label are anodized metal substrates affixed to a surface of the core.

Example 21 can include subject matter such as a method of labeling an implantable medical device. The method comprises coupling a first biocompatible metal substrate and a second biocompatible metal substrate to a core of a header of the implantable medical device, the core having a first bore and a second bore, wherein the first biocompatible metal substrate is positioned adjacent to the first bore and the second biocompatible metal substrate is positioned adjacent to the second bore, anodizing the first biocompatible metal substrate to include at least a first color, anodizing the second biocompatible metal substrate to include at least a second color, the second color different from the first color, and overmolding the core including the first biocompatible metal substrate label and the second biocompatible metal substrate.

Example 22 can include, or can optionally be combined with the subject matter of one or any combination of Examples 1-21, to optionally include where anodizing the first biocompatible metal substrate and anodizing the second biocompatible metal substrate are done prior to affixing the first biocompatible metal substrate and the second biocompatible metal substrate to the core. Example 23 can include, or can optionally be combined with the subject matter of one or any combination of Examples 1-22, to optionally include anodizing the first biocompatible metal substrate and anodizing the second biocompatible metal substrate are done using at least one of electrochemical anodizing and LASER anodizing.

Example 23 can include, or can optionally be combined with the subject matter of one or any combination of Examples 1-22, to optionally include coupling a first lead of a lead assembly to the first bore, and coupling a second lead of a lead assembly to the second bore.

Example 24 can include, or can optionally be combined with the subject matter of one or any combination of Examples 1-23, to optionally include anodizing a first annular ring to include the first color, anodizing a second annular ring to include the second color, coupling the first annular ring to a proximal end of the first lead, and coupling the second annular ring to a proximal end of the second lead.

Example 25 can include, or can optionally be combined with the subject matter of one or any combination of Examples 1-24, to optionally include forming the core to include a first receiving cavity and a second receiving cavity, the first receiving cavity configured to receive the first biocompatible metal substrate and the second receiving cavity configured to receive the second biocompatible metal substrate.

Example 26 can include, or can optionally be combined with the subject matter of one or any combination of Examples 1-25, to optionally include anodizing a first contact wire extending from a housing including electronic circuitry to include the first color, anodizing a second contact wire extending from the housing to include the second color, coupling the first contact wire to the a connector block positioned within the first bore, and coupling the second contact wire to a connector block positioned within the second bore.

Example 27 can include, or can optionally be combined with the subject matter of one or any combination of Examples 1-26, to optionally include anodizing the first biocompatible metal substrate to include a first text, and anodizing the second biocompatible metal substrate to include a second text, the second text different from the first text.

Example 28 can include, or can optionally be combined with the subject matter of one or any combination of Examples 1-27, to optionally include where anodizing the first biocompatible metal substrate to include the first color and anodizing the second biocompatible metal substrate to include the second color are done using a electrochemical anodizing process, and wherein anodizing the first biocompatible metal substrate to include the first text and anodizing the second biocompatible metal substrate to include the second text are done using a LASER anodizing process.

A method of labeling an implantable medical device, the method comprising:

Example 29 can include subject matter such as a method of labeling an implantable medical device. The method can include coupling a biocompatible metal substrate to a core of a header of the implantable medical device, the core having a first bore and a second bore, anodizing a first portion of the biocompatible metal substrate to include a first color, anodizing a second portion of the biocompatible metal substrate to include a second color, the second color different from the first color, wherein the first portion of the biocompatible metal substrate is positioned adjacent to the first bore and the second portion of the biocompatible metal substrate is positioned adjacent to the second bore, and overmolding the core including the first biocompatible metal substrate label and the second biocompatible metal substrate.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An implantable medical device, comprising:
    a housing including electronic circuitry;
    a header coupled to the housing and including a core, the core including:
        a bore; and
        a connector block opening in communication with the bore;
        a receiving cavity positioned adjacent to the bore;
        a window in communication with the receiving cavity;
        a connector block positioned within the connector block opening and including a first identifier; and
        a contact wire extending from the housing, the contact wire including the first identifier and configured to couple to the connector block.

2. The implantable medical device of claim 1, wherein the first identifier is a color.

3. The implantable medical device of claim 1, further including:
    a metal label positioned within the first receiving cavity and including the first identifier.

4. The implantable medical device of claim 3, wherein the first identifier on the metal label is visible through the window.

5. The implantable medical device of claim 4, wherein the metal label is a first metal label, the device further including:
    a lead including a second metal label including the first identifier, wherein the lead is configured to be electrically coupled to the electronic circuitry via the connector block and the contact wire.

6. An implantable medical device, comprising:
    a housing including electronic circuitry;
    a header coupled to the housing and including a core having a first face, a second face opposite the first face, a first side wall, and a second side wall opposite the first side wall, the core including:
        a first bore extending from the first side wall toward the second side wall;
        a first connector block opening in communication with the first bore;
        a first receiving cavity extending from the first side wall toward the second side wall, the first receiving cavity positioned adjacent to the first bore; and
        a first window extending from the first face to the receiving cavity such that the first window is in communication with the receiving cavity;
        a first connector block positioned within the first connector block opening, wherein the first connector block includes a first identifier; and
        a first contact wire extending from the housing, the first contact wire including the first identifier and configured to couple to the first connector block.

7. The implantable medical device of claim 6, further including:
    a first metal label positioned within the first receiving cavity adjacent to the first bore, wherein the first metal label includes the first identifier.

8. The implantable medical device of claim 7, wherein the first identifier is a color.

9. The implantable medical device of claim 7, wherein the core further includes:
    a second bore extending from the first side wall toward the second side wall;
    a second receiving cavity extending form the first side wall toward the second side wall, the second receiving cavity positioned adjacent to the second bore;
    a second window extending from the first face to the receiving cavity such that the second window is in communication with the second receiving cavity; and
    a second connector block opening in communication with the second bore.

10. The implantable medical device of claim 9, further including:
    a second metal label positioned within the second receiving cavity adjacent to the second bore, wherein the second metal label includes a second identifier;
    a second connector block positioned within the second connector block opening, wherein the second connector block includes the second identifier, the second identifier different from the first identifier; and
    a second contact wire extending from the housing, the second contact wire including the second identifier and configured to couple to the second connector block.

11. The implantable medical device of claim 10, further including:
    a lead assembly including a first lead and a second lead, wherein the first lead includes a first metal label including the first identifier and is configured to be electrically coupled to the electronic circuitry via the first connector block and the first contact wire, and the second lead includes a second metal label including the second identifier and is configured to be electrically coupled to the electronic circuitry via the second connector block and the second contact wire.

12. The implantable medical device of claim 10, wherein the first metal label and the second metal label are chosen from at least one of titanium, tantalum, tungsten, and stainless steel.

13. The implantable medical device of claim 6, wherein the core is overmolded with a dielectric material.

14. The implantable medical device of claim 6, wherein the first receiving cavity has a first area that is greater than a second area of the first window.

* * * * *